United States Patent [19]

Levinson et al.

[11] 3,952,728

[45] Apr. 27, 1976

[54] METHOD OF MEASURING DYNAMIC (A) AUDITORY AND (B) TACTILE SEQUENCING OR TRACKING, AND DIAGNOSING CEREBELLAR-VESTIBULAR DYSFUNCTION AND DYSMETRIC DYSLEXIA

[76] Inventors: Harold N. Levinson, 15 Lake Road, Great Neck, N.Y. 11020; Jan Frank, 45 E. 82nd St., New York, N.Y. 10028

[22] Filed: Feb. 24, 1975

[21] Appl. No.: 552,700

Related U.S. Application Data

[63] Continuation-in-part of Ser. No. 535,507, Dec. 23, 1974, abandoned.

[52] U.S. Cl. ............................... 128/2 R; 128/2 N; 128/2 Z
[51] Int. Cl.² .......................................... A61B 5/00
[58] Field of Search ............ 128/2 Z, 2 R, 2 T, 2 N, 128/2 S, 2.1 M, 2.1 R

[56] References Cited
UNITED STATES PATENTS

| | | | |
|---|---|---|---|
| 3,000,271 | 9/1961 | Harvey et al. | 128/2.1 M |
| 3,030,944 | 4/1962 | Blau et al. | 128/2 N |
| 3,842,822 | 10/1974 | Levinson et al. | 128/2 R |

Primary Examiner—Kyle L. Howell
Attorney, Agent, or Firm—Bauer, Amer & King

[57] ABSTRACT

The discovery that the condition of dysmetric dyslexia results from dysfunctioning of the cerebellar-vestibular underlies the method of U.S. Pat. No. 3,842,822 issued on Oct. 22, 1974, which method uses blurring and scrambling of sequential visual stimuli to identify and measure ocular motor coordination, i.e. ocular fixation and sequential scanning abilities.

As an improvement and/or alternative to the above method, the within methods, which also are useful in identifying dysmetric dyslexic children in an examination group, use response to acoustical and/or tactile stimulation, rather than response to visual stimuli, to identify said condition.

12 Claims, 4 Drawing Figures

METHOD OF MEASURING DYNAMIC (A) AUDITORY AND (B) TACTILE SEQUENCING OR TRACKING, AND DIAGNOSING CEREBELLAR-VESTIBULAR DYSFUNCTION AND DYSMETRIC DYSLEXIA

This is a continuation-in-part of application Ser. No. 535,507, filed Dec. 23, 1974, now abandoned.

The present invention relates to conveniently administered methods of identifying members of an examination group who are possibly dysmetric dyslexic, and more particularly monitors the response to acoustical and tactile stimulation of the group members so as to both provide the identification being sought, and also to obtain a measurement of the impairment or extent of dysfunctioning of the cerebellar-vestibular of those members who are identified as dysmetric dyslexic.

An impaired cerebellar-vestibular apparatus cannot neutralize or inhibit or "slow down" rapid or fast moving incoming sequential stimuli of a visual nature and thus leads to cortical or perceptual confusion or scrambling. In a screening method using incoming visual stimuli, of U.S. Pat. No. 3,842,822, issued on Oct. 22, 1974, the impairment of the cerebellar-vestibular is manifested by a blurring or scrambling of the visual stimuli under conditions at which "normal" children do not similarly experience these effects.

Underlying the present invention is the recognition that a dysmetric dyslexic child, because of his cerebellar-vestibular dysfunction, also responds in a characteristically different way to non-visual sensory input, and so may also be effectively indentified by such response. The methods hereof are practiced using (a) acoustical or auditory material, and (b) tactile stimulation, as said non-visual sensory input. Since the reason for the effectiveness of the inventive methods is the same for both aforesaid forms of non-visual sensory input, the explanation thereof which follows, although specifically related to acoustical or auditory material, is suffice to provide a complete understanding of the present invention.

It has been known, but heretofore never used for screening, identification or the like, that dysmetric dyslexic children frequently reverse the phonetic sequence of sounds while speaking and often have difficulty blending phonetic sequences in words and letters they see. When attempting to sound out and blend the phonemes in a word, they frequently skip over one or two in a sequence of three or four, and even reverse the whole sequence or phonetic pairs within a word. They even occasionally have difficulty matching, recalling or coordinating the sound of a letter with its visual form. These difficulties were thought to be cortical, since it was not fully appreciated that the cerebellar-vestibular controls sensory input. Rather, the prevalent belief was that the cerebellar-vestibular only controlled motor functions or performance. It is now demonstrated that this is not the case. Moreover, an important contribution of the present invention is the utilization of the foregoing as a basis for a test and procedure to diagnose on an individual and mass basis cerebellar-vestibular dysfunction and dysmetric dyslexia. More particularly, the within auditory test and procedure is effective because of a failure to identify "dynamic" or sequentially-presented auditory stimuli, even though the individuals that exhibit the failure have normal sufficient auditory acuity, and thus would perform well taking a conventional hearing test.

The cerebellar-vestibular circuits slow down the auditory material input rate, maintain the order of incoming sequential stimuli before sending them up to the cortex for interpretation, perception or recognition, and coordinate the various sensory inputs.

When the cerebellar-vestibular circuits are impaired, the order of the incoming sequential stimuli cannot be maintained and the rate cannot be properly slowed down prior to their transmission to the cortex, and the various sensory stimuli cannot be coordinated in time and space.

In said U.S. Pat. No. 3,842,822, we have demonstrated that blurring and scrambling of sequential visual stimuli occurs at significantly lower input speeds in children with cerebellar-vestibular dysfunction and dysmetric dyslexia than in normal children. By analogy to the visual or ocularmotor model, the acoustical response test hereof owes its effectiveness to its being related to the ability of the individual being tested to handle incoming auditory stimuli. That is, when there is poor performance, it is as if the auditory fixation and sequential scanning functions were impaired. Increasing the rate of incoming and sequential auditory stimuli leads, by analogy, to an auditory ataxia or nystagmus and auditory scrambling occurs. Thus, by speeding up the rate of presentation of sounds, e.g. letters, words or sentence sequences to an examination group, a speed is reached where "sound scrambling" or "blurring" occurs. The speed at which this auditory scrambling or blurring occurs is significantly less for children with cerebellar-vestibular dysfunction than for those without cerebellar-vestibular dysfunction.

Similar in concept to the above, the within invention also contemplates utilizing a dynamic sequential tactile test where tactile sequential stimuli are speeded up to the point where tactile scrambling or blurring occurs. By definition, said point is that at which the tactile pattern can no longer be perceived as a Gestalt. For example, a pattern of two or three sequential pinpricks or other sensations applied to the skin, when speeded up, may then be perceived as one, during tactile scrambling or blurring. By way of further example, for tactile sequential scanning, one can picture utilizing the sticks of a xylophone touching separate areas of the skin in a sequence of four beats — one, two, three, four — the beats are then speeded up, faster and faster, until there is a point where the cortex can no longer distinguish four, but, during the scrambling or blurring, feels only one.

The explanation for the blurring of both the aforesaid forms of non-visual stimuli is that the cerebellar-vestibular cicuits have been unable to slow down the rate and maintain the order of incoming sequential stimuli before sending them up to the cortex for interpretation, perception or recognition. When the cerebellar-vestibular circuits are impaired, as is the situation with dyslexic children, the order of the incoming sequential stimuli cannot be maintained and the rate cannot be properly slowed down prior to their transmission to the cortex at significantly lower speed levels than with normal children. In addition, audio or tactile stimuli are not properly coordinated or synchronized prior to cortical transmission. As a result, the stimuli are transmitted to the cortex at a rate and in a scramble beyond the cortical perception or recognition threshold.

Broadly, it is an object of the present invention to provide an effective method for screening comparatively large groups of children, even of pre-school age, to determine which of those may possibly be dysmetric dyslexic. Specifically, it is an object to achieve, by the administration of said screening test, not only the identification of dysmetric dyslexic children, but also an indication of the extent of impairment of the cerebellar-vestibular apparatus of such children.

One form of a diagnostic screening procedure for identifying those in an examination group possibly having the condition of dysmetric dyslexia, demonstrating objects and advantages of the present invention, contemplates the step of reciting words at a selected volume level and in a language known to said group for the purpose of requiring identification of said recited words by members of said group. Simultaneously with this recitation of words, there is also presented in background relation thereto, auditory material which is initially at a volume at a selected volume level below that of the recited words. The volume level of the background auditory material, however, is progressively increased while the group continues its efforts to identify the recited words. Any group member unable to make said identification of recited words because of inability to suppress the background auditory material is automaticallly identified as possibly being dysmetric dyslexic.

In another form of testing procedure according to the present invention, the rate of the recited words is progressively increased to pressure the ability of the listeners, and thus their cerebellar-vestibular apparatus, to achieve proper identification of the recited words. Here also, the performance of dysmetric dyslexic children is significantly different from "normal" children.

In still another contemplated form of testing procedure, the patient is tested with tactile stimulation, the same being in the specific form of a progressively increased pattern of an intermittently produced elevated temperature applied with a skin-contacting surface. Dyslexic children will perceive the test stimulation as an uninterrupted heat source, i.e. one without a changing pattern, at a significantly lower rate of application than normal children.

The above brief description, as well as further objects, features and advantages of the present invention, will be more fully appreciated by reference to the following detailed description of the inventive methods herein and of apparatus for practicing the same, when taken in conjunction with the accompanying drawings, wherein.

DYNAMIC AUDITORY STIMULATION

Figure 1:
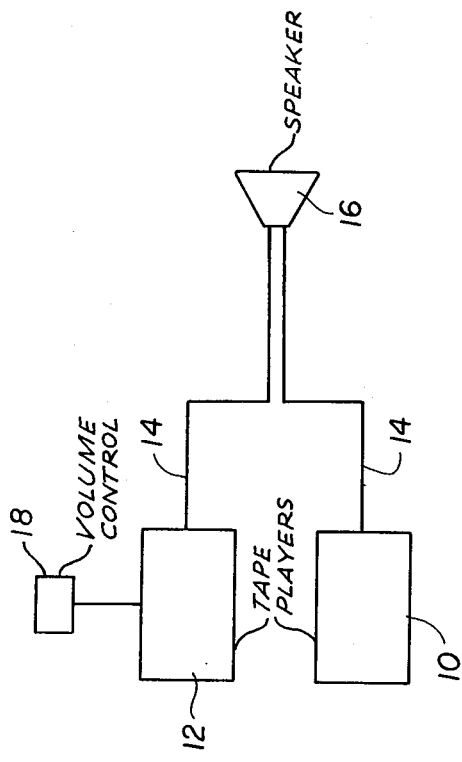
FIG. 1 is a diagramatic view of exemplary apparatus for presenting auditory materials during practice of the methods of the present invention.

Equipment which may effectively be used to identify individuals who are dysmetric dyslexic by the manner in which these individuals respond to auditory materials presented to them may take a variety of forms, and may consist of any one of numerous models of sound-producing equipment. For example, as illustrated in FIG. 1, the within method, which will soon be described in detail, may be practiced using two conventional record or tape players 10, 12 appropriately connected via conductors 14 to produce sound through a speaker 16. Alternatively, the players 10, 12 can be hooked up to present the auditory content of records or tapes to a number of earphones, each of which is worn by a member of the examination group being tested or screened by the equipment of FIG. 1. Completing the illustrated arrangement is a volume control unit 18 associated with the player 12.

Generally the equipment just described in connection with FIG. 1 would be operated according to the method of the within invention in the following manner. Player 10 would broadcast through speaker 16 the auditory content of a cassette or tape which will consist, in a preferred embodiment, of words recited one after the other, in the English language or, in any event, a language known to the examination group, which primarily will consist of young children ranging in age from three to ten years. The recited words broadcast by the player 10 is conveniently referred to as foreground auditory material. This material will be presented at a selected volume level which will not be varied during the practice of the within method.

During the presentation of the foreground auditory material by the player 10, player 12 will simultaneously present what can be referred to as background auditory material. This material consists of the content of a cassette or the like being played by the player 12 and also presented to the group through the speaker 16. This background material will start initially at a volume level which is significantly less than the volume level of the foreground auditory material but which, in accordance with the present invention, is progressively increased until it approaches the volume level of the foreground auditory material. To provide this variation in volume level use is made of the level control unit 18 during the operation of the player 12.

The significance of the foregoing is that members of the examination group are required to identify the foreground auditory material despite the distraction caused by the background auditory material. The effectiveness of the individual members of the group to make the identification has a relationship to dysmetric dyslexia insofar as a healthy and properly functioning cerebellar-vestibular is required in order to make said identification. That is, dysmetric dyslexia, as already indicated, is a condition caused by a dysfunctioning cerebellar-vestibular, and said dysfunction results in an inability of the individual to suppress the distraction caused by the background auditory material so that proper identification can be made of the foreground auditory material. It therefore follows that a member unable to make this suppression in all probability has dysfunctioning cerebellar-vestibular, and consequently also suffers from dysmetric dyslexia.

Figure 2:
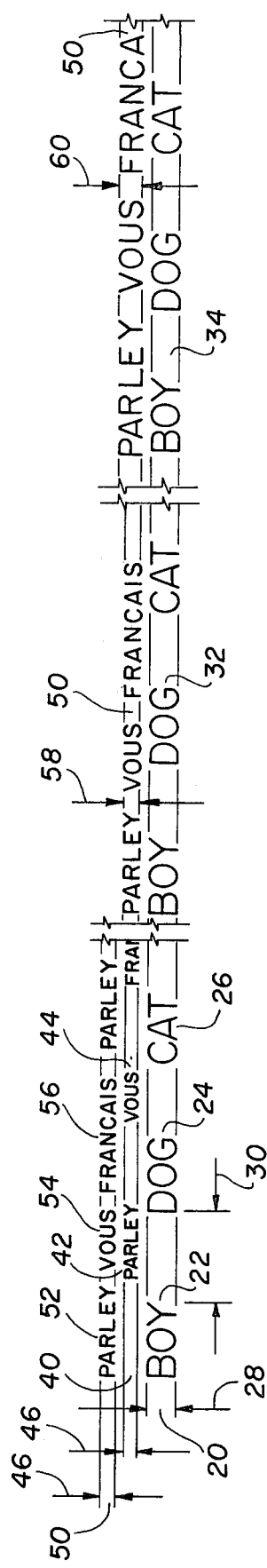
FIG. 2 is a graphic representation of the manner in which the auditory materials are presented when the within methods are practiced.

Reference should now be made to FIG. 2 wherein there is a graphic representation of the manner in which the auditory material is presented to the examination group. Specifically, the foreground auditory material, designated generally by the reference numeral 20, consists, as indicated above, of common words recited one after the other, as exemplified by the word "boy" designated 22, the word "dog" 24 and the word "cat" 26. The vertical dimension of these words is intended to illustrate the volume level 28 at which these words are presented to the examination group. During the practice of the within method, following the recitation of word 22, there is a selected time interval 30, of perhaps one or two seconds, which is followed by the recitation of the word 24, then the word 26, and then possibly other common words. Following the recitation of this sequence of words at the volume level 28, the sequence is repeated at the same volume thereby providing word recitation repetitions 32, 34, and so forth.

During presentation of the foreground auditory material 20, the within screening method contemplates use of background auditory material as a distraction which interferes, in a controlled manner, with identification of the foreground auditory material. Such background auditory material, in one preferred form designated generally by the reference numeral 40, consists of words in a foreign language or a language in any event which is not known to members of the examination group. This material may consist of the French word "parley" 42 and "vous" 44. A most significant aspect of the background material 40 is that it is presented initially at volume level 46 which is significantly less than volume level 28 of the foreground auditory material 20. During the practice of the within method, however, volume level 46 is progressively increased until it approaches volume level 28. The form of background auditory material 40 just described also contemplates presentation of the words 42 and 44 in the time interval 30 which exists between succeeding foreground adjacent words 22 and 24.

Another form of background auditory material which is effectively used in accordance with the present invention is that designated generally by the reference numeral 50. This auditory material also consists of words of a foreign language, as exemplified by the words 52, 54 and 56, the same being presented initially at the previously noted diminished volume level 46. The background auditory material 50 differs from background auditory material 40, however, in that the words 52, 54 and 56 thereof are presented not only in the time interval 30 but in superimposed relation to the foreground recited words 22, 24 and 26, and so on.

Still referring to FIG. 2 and using the auditory material 50 as the example, it is shown in that figure that the repeats of this material are made at progressively increasing volume levels, such as volume levels 58 and 60.

Normal children and individuals, i.e. those children and individuals whoe are not dysmetric dyslexic, have no difficulty in suppressing the distracting background auditory material 40, 50, and consequently making proper identification of the foreground auditory material 20. Ultimately, when the volume level of the background material 50 reaches the level 60 which will be understood to be almost the level 28 of the foreground auditory material 20, some difficulty may be experienced even by normal children and individuals. However, children and individuals whoe are dysmetric dyslexic are unable to make proper identification of the foreground auditory material 20 even when the background auditory material is at a significantly diminished volume level, as exemplified by level 46. These dysmetric dyslexic children may typically identify the foreground word 22 and next identify the foreground word 26, missing entirely the intermediate foreground word 24. In some instances, the dysmetric dyslexic child may fail to identify several of the foreground auditory words 20 and, in some instances may totaly fail to identify any of the words in a specific sequence.

In the screening and identification method of U.S. Pat. No. 3,842,822, we are able to effectively identify members of an examination group who are dysmetric dyslexic. In the method of the present invention, the performance of a member of the examination group in making identification of the foreground auditory material 20 is also significant in determining if he is dysmetric dyslexic. If he is, it additionally is a measure of the extent of impairment or dysfunctioning of the cerebeller-vestibular of this member. As may readily be appreciated, if the failure in the identification of the foreground material 20 consists of isolated instances of missing only one word thereof, this would indicate an impairment or dysfunctioning of the cerebellar-vestibular which is not as severe or in as an advanced stage as when the failure in the identification consists of missing many words of the recited sequence, or possibly even failing to identify any of the words in a sequence.

The method for identifying dysmetric dyslexia based on acoustical responses of an examination group, as just described, can be modified. For example, instead of using recited words as background auditory material 40, 50, and thus material of the same quality as the foreground auditory material 20, use can effectively be made of music or a different quality sound as the background auditory material, and still provide an effective method of screening out members of an examination group who may possibly be dysmetric dyslexic. Also, as already indicated, the method herein is not one which measures the hearing ability of an individual, but rather it measures the ability of such person, and more particularly the cerebellar-vestibular circuits of this person, in handling auditory stimuli. Specifically, it measures the ability of the cerebellar-vestibular to transmit to the brain auditory stimuli in the same sequence in which it is presented to the individual. In this respect, auditory material 20 can be presented as recited words 22, 24, etc. with an initial time interval 30 therebetween, and then this time interval can be progressively diminished until the succeeding words are recited almost one upon the other. Recitation in this manner also requires concentration on the part of the listener and, more particularly, a properly functioning cerebellar-vestibular to enable identification by the listener of the recited words in the sequence in which they are recited. Here again, individuals whoe are dysmetric dyslexic have more difficulty, which can be readily recognized, than "normal" individuals in maintaining a recognition of a rapid recitation of words. In a sense, therefore, the time intervals 30 between adjacent words 22, 24 are a form of background and the variation thereof influences recognition or identification of the recited words, all in a way of permitting the identification of individuals who may be dysmetric dyslexic.

In the just mentioned screening and diagnostic test, in addition to progressively diminishing the time intervals 30, a background distraction can also be used to test the patient for a healthy and properly functioning cerebellar-vestibular apparatus. Said background distraction can take many forms, such as music or a foreign language. When using a background sound, the test is thus intensified, since proper identification by the patient requires a cerebellar-vestibular which can keep in proper sequence the words 22, 24 being more progressively rapidly recited during the testing interval, and also one which can properly suppress or block out the distraction caused by the background auditory material. Regarding said background, it can be of a fixed volume level, or it can be of an initial low volume level and progressively increased, depending on what extent it is desired to interfere, in a controlled manner as herein described, with the examination group's efforts to identify the foreground test words.

DYNAMIC TACTILE STIMULATION

Figure 3:
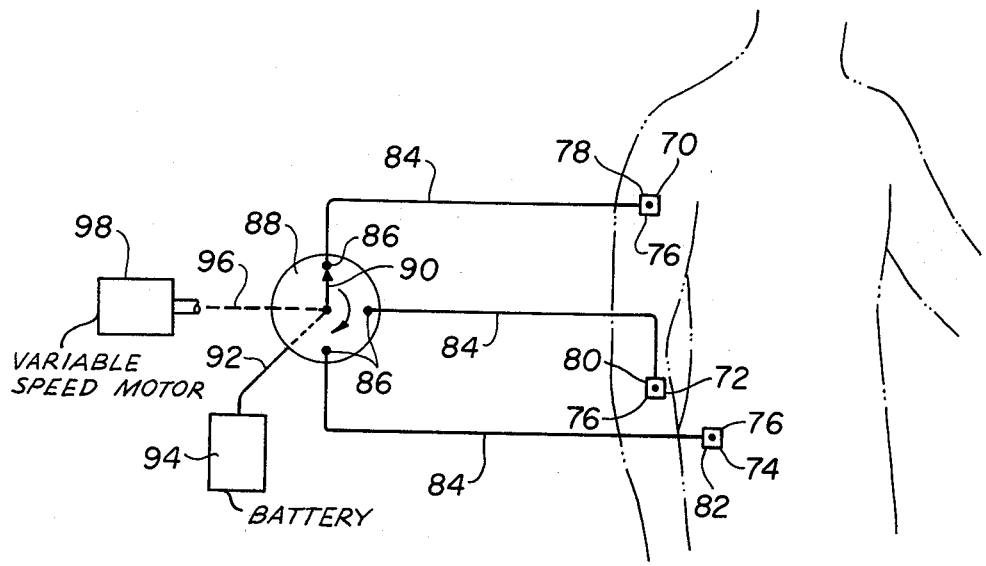
FIGS. 3 and 4, like FIG. 1, are diagramatic views of two exemplary embodiments of apparatus for practicing methods of the present invention, wherein tactile rather than auditory stimulation is utilized.
Figure 4:
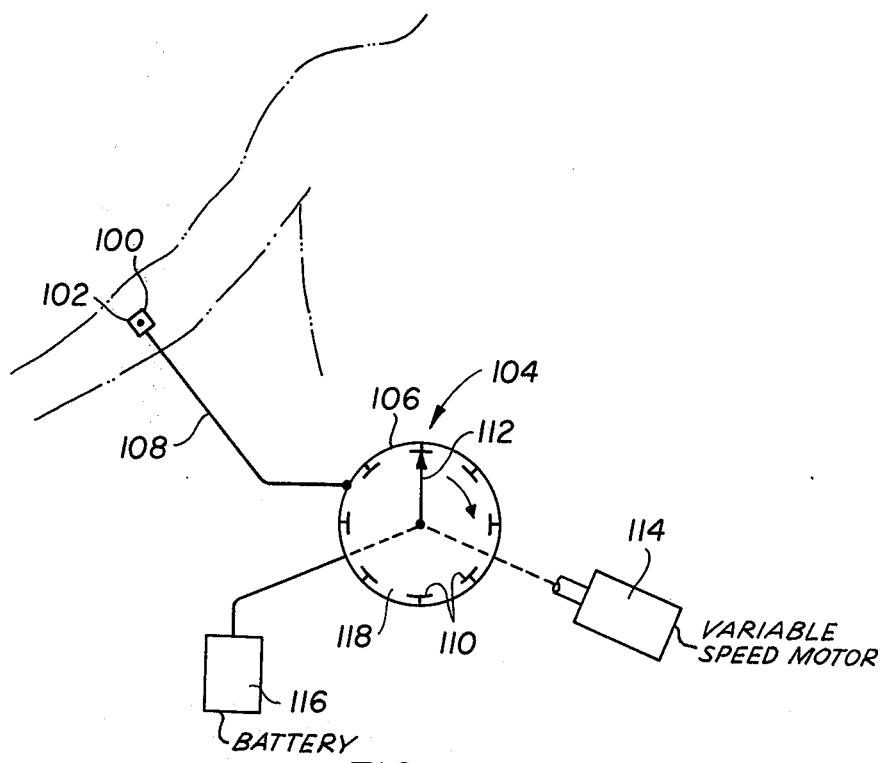

Reference is now made to FIGS. 3 and 4 which illustrate apparatus for practicing methods of identifying during the screening of patients, those who have cerebellar-vestibular dysfunction and dysmetric dyslexia. The methods, and apparatus for their practice, may take many forms, only two of which are respectively illustrated in FIGS. 3 and 4. These various methods, however, have a common concept, which is similar to that already expressed in connection with the dynamic auditory stimulation methods of FIGS. 1 and 2. Specifically, this concept is that dysmetric dyslexic children, because of their cerebellar-vestibular dysfunction, respond in a characteristically different way than normal children to stimuli, whether it be auditory or tactile. This response will now be described in detail in connection with two exemplary methods and apparatus for their practice, which utilize tactile stimulation and which are illustrated in FIGS. 3 and 4.

In FIG. 3, reference numerals 70, 72 and 74 identify an electrically operated element commonly known as a thermistor, which is commercially available from many sources, including General Electric. As is generally understood, the thermistor has a large thermal co-efficient of resistance, such that when energized electrically, the resulting current flow through the body of the thermistor results in a flat contact surface, designated 76, of the component reaching an elevated temperature significantly above ambient temperature. In the present application, it will be understood that surface 76 is appropriately placed in contact with the patient's skin by any appropriate means, as by being adhesively taped thereto, at the locations illustrated. These locations may typically be location 78 at the upper portion of the arm, location 80 at the forearm, and location 82 at the patient's waist. Each of the thermistor components are connected by a conductor 84 to a cooperating contact 86 of a switching device 88 having a rotatable contact arm 90. Contact 90 is electrically connected by a conductor 92 to a source of electricity which may be a battery 94, and is also appropriately mechanically connected, as by a shaft connection 96, to be powered in rotation by variable speed motor 98.

In operation, every time that contact arm 90 makes electrical contact with a contact 86, the energizing circuit for the thermistor component associated with that contact is completed to the battery source 94, with the result that there is current flow to the thermistor component and an increase in temperature in the contact surface 76 of that component. Since the contact arm 90 is driven in rotation by the variable speed motor 98, the components 70, 72 and 74 apply a sensation of an elevated temperature in a succeeding fashion during each revolution or sweep of the contact arm 90. In accordance with the present invention, it is contemplated that this successively applied sensation of an elevated temperature, for tactile stimulation, be progressively increased during the testing interval. This is readily achieved by increasing the speed at which variable motor 98 drives the contact arm 90 in rotation.

In practice, it has been found that dysmetric dyslexic children perceive the tactile stimulation, which in reality is at all times of an intermittent nature, i.e. applied only when contact arm 90 is in electrical contact with contact 86 and not during its travel between these contacts, as a steady, continuously applied stimulation at a significantly lower speed of operation of the motor 98 than normal children. Stated another way, at a much lower rate of operation of the motor 98, the intermittent nature of the tactile pattern can no longer be perceived as a Gestalt by the dyslexic children, whereas normal children have no difficulty perceiving the intermittent pattern of the tactile stimulation until the rate of operation of the motor 98 is quite high.

FIG. 4 illustrates another form of apparatus for practicing the tactile stimulation test of FIG. 3. In this embodiment of apparatus, and therefore in the method which it practices, use is made of only one location for the thermistor component 100, the same being on the patient's forearm at location 102. Switching device 104 used in this method procedure includes outer contact ring 106 which the thermistor 100 is connected to via the conductor 108. Concentrically spaced apart contacts, individually and collectively designated 110, are connected to the ring 106 and in turn are electrically contacted by the rotating contact arm 112 which is driven in rotation by the variable speed motor 114. It is only when contact arm 112 is in electrical contact with a contact 110 that a battery 116 charges the thermistor component 100 and thereby produces an elevated temperature sensation which is transmitted to the patient. Since the contacts 110 are discontinuous, i.e. separated by the space 118, the tactile stimulation received by the patient should be of an intermittent pattern. This initially is the case for both normal children and children who are dysmetric dyslexic. However, at a significantly lower speed of operation of the motor 114, the dysmetric dyslexic children perceive the tactile stimulation as a continuously applied temperature because of the "blurring" or tactile scrambling that is produced by the dysfunction of their cerebellar-vestibular circuits.

A latitude of modification, change and substitution is intended in the foregoing disclosure, and in some instances some features of the invention will be employed without a corresponding use of other features. Accordingly, it is appropriate that the appended claims be construed broadly and in a manner consistent with the spirit and scope of the invention herein.

What is claimed is:

1. A group diagnostic screening procedure for identifying those in said group possibly having the condition of dysmetric dyslexia, which is based on the discoveries of a cerebellar-vestibular dysfunction and resulting impaired accoustical suppression by said cerebellar-vestibular indicative of said condition, said prcedure comprising the steps of reciting words at a selected volume level and in a language known to said group for the purpose of requiring identification of said recited words by members of said group, simultaneously with the aforesaid recitation of words causing in background relation thereto auditory material to be presented to said group starting at a volume at a selected level below that of said recited words, and progressively increasing the volume level of said background auditory material while requiring said identification of said recited words by said group members, whereby any group member unable to make said identification of recited words because of improper suppression of said background auditory material is automatically identified as possibly being dysmetric dyslexic.

2. The dysmetric dyslexia diagnostic screening procedure as defined in claim 1 wherein said background auditory material also consists of recited words, but in a language foreign to said group, whereby the quality of the auditory material presented to said group is generally similar.

3. The dysmetric dyslexia diagnostic screening procedure as defined in claim 1 wherein music is used as said background auditory material.

4. The dysmetric dyslexia diagnostic screening procedure as defined in claim 1 wherein each succeeding recited word is presented after a selected time interval, and said background auditory material is presented during said time interval.

5. A group diagnostic screening procedure for identifying those in said group possibly having the condition of dysmetric dyslexia, which is based on the discovery of a cerebellar-vestibular dysfunction and resulting impaired response to acoustical input indicative of said condition, said procedure comprising the steps of reciting words to said group for the purpose of requiring their identification, presenting each said succeeding recited word after a selected time interval, and progressively diminishing the duration of said time interval while requiring said identification of said recited words by said group members, whereby any group member unable at an early stage of said recitation of words to make an identification thereof is automatically identified as possibly being dysmetric dyslexic.

6. The dysmetric dyslexia diagnostic screening procedure as defined in claim 5 wherein said recited words are of a selected nominal number and are presented in a repeating sequence.

7. The dysmetric dyslexia diagnostic screening procedure as defined in claim 6 wherein music is used as background auditory material.

8. The dysmetric dyslexia diagnostic screening procedure as defined in claim 6 wherein a foreign language is used as background auditory material.

9. A diagnostic screening procedure for identifying the condition of dysmetric dyslexia, which is based on the discovery of a cerebellar-vestibular dysfunction and resulting impaired response to tactile input indicative of said condition, said procedure comprising the steps of applying an intermittent pattern of tactile stimulation to a patient being screened in a repeating cycle, progressively increasing the cylical rate of application of said patterned tactile stimulation, and automatically identifying a patient being screened as possibly being dysmetric dyslexic who perceives said intermittent pattern as a continuously applied stimulation at an early stage during the test interval.

10. A diagnostic screening procedure for identifying the condition of dysmetric dyslexia using tactile stimulation as defined in claim 9, wherein alternate sensations of an elevated temperature followed by an interval of ambient temperature in a cyclically repeated sequence is utilized as said tactile stimulation.

11. A diagnostic screening procedure for identifying the condition of dysmetric dyslexia using tactile stimulation as defined in claim 10, wherein said tactile stimulation is applied at a single selected location on the patient.

12. A diagnostic screening procedure for identifying the condition of dysmetric dyslexia using tactile stimulation as defined in claim 10, wherein said tactile stimulation is applied at plural selected locations on the patient.

* * * * *